United States Patent [19]

Boehlke et al.

[11] Patent Number: 4,510,323

[45] Date of Patent: Apr. 9, 1985

[54] CIS-BICYCLO[3.3.0]OCTANE DERIVATIVES, MEDICAMENTS CONTAINING THEM AND PROCESSES FOR THEIR PREPARATION AND USE

[75] Inventors: Horst R. E. Boehlke; Gerriet K. H. Loschen, both of Stolberg; Gudrun E. Michel, Aachen; Bernd Müller, Roetgen, all of Fed. Rep. of Germany

[73] Assignee: Gruenenthal GmbH, Stolberg, Fed. Rep. of Germany

[21] Appl. No.: 442,240

[22] Filed: Nov. 17, 1982

[30] Foreign Application Priority Data

Nov. 21, 1981 [DE] Fed. Rep. of Germany ....... 3146278

[51] Int. Cl.³ .................. C07C 69/76; C07C 65/24
[52] U.S. Cl. ..................... 514/530; 560/56;
    549/333; 549/336; 568/327; 562/466; 514/569
[58] Field of Search ............ 562/466; 560/56;
    424/308, 317

[56] References Cited

FOREIGN PATENT DOCUMENTS 201699 10/1979 United Kingdom .

Primary Examiner—Paul J. Killos
Attorney, Agent, or Firm—Schwartz, Jeffery, Schwaab, Mack, Blumenthal & Koch

[57] ABSTRACT

Cis-bicyclo[3.3.0]octane derivatives corresponding to the formula

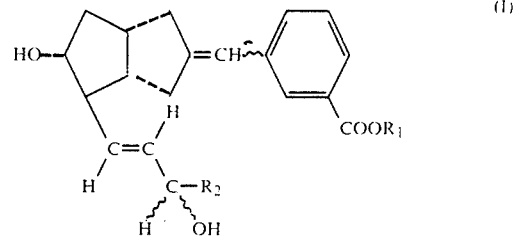

wherein $R_1$ is hydrogen, a lower alkyl group or a cation and wherein $R_2$ represents a cyclohexyl or an adamantyl group. In these compounds the phenyl radical may be arranged with respect to the double bond in the EZ- or in the E-configuration and at the carbon atom bearing the group $R_2$ the molecule may have the RS- or S-configuration. The compounds are prepared by reacting compounds of the formulae

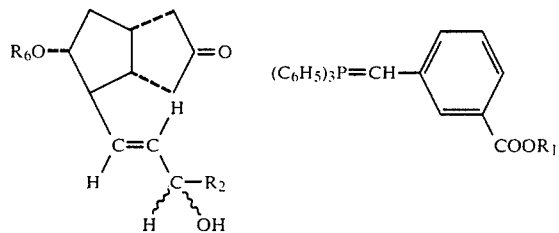

wherein $R_1$ and $R_2$ have the same meaning as above and $R_6$ represents hydrogen or a protecting group. Medicaments containing these compounds act as inhibitors of blood platelet aggregation and (in higher doses) as blood pressure lowering agents.

25 Claims, No Drawings

CIS-BICYCLO[3.3.0]OCTANE DERIVATIVES, MEDICAMENTS CONTAINING THEM AND PROCESSES FOR THEIR PREPARATION AND USE

BACKGROUND OF THE INVENTION

The present invention relates to new cis-bicyclo[3.3.0]octane derivatives, to pharmaceutical compositions containing these new compounds for oral or parenteral administration and also to processes for preparing these new compounds and for using the compositions. The new cis-bicyclo[3.3.0]octane derivatives according to the invention correspond to the general formula:

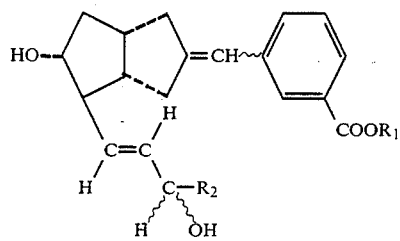

in which the phenyl radical has the EZ- or the E-configuration with respect to the double bond and in which the carbon atom which at carried the group $R_2$ (and others) the molecule has the RS- or S-configuration.

In formula I, $R_1$ represents a hydrogen atom, a straight or branched alkyl group containing 1 to 4 carbon atoms or a pharmaceutically acceptable cation. Preferably $R_1$ represents hydrogen, a methyl or an ethyl radical or, if it represents a cation, a sodium or a potassium cation. Other suitable cations are known from their use in the chemistry of prostaglandins or prostacyclin, respectively.

$R_2$ represents a cyclohexyl or 4-methyl cyclohexyl radical or a 1-adamantyl group of the formula:

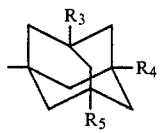

wherein $R_3$, $R_4$ and $R_5$ have the same or a different meaning and each represents hydrogen or methyl.

Preferably the radicals $R_3$ to $R_5$ represent hydrogen. In preferred compounds of formula I, $R_2$ represents the group:

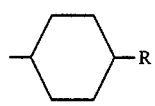

wherein R is hydrogen or methyl. The unsubstituted cyclohexyl group (R=H) is especially preferred.

The compounds of formula I have valuable pharmacological properties. In particular, they have blood platelet aggregation inhibiting effects (in-vitro and in-vivo) and also blood pressure lowering activity, i.e. they have prostacyclin-like properties. They distinguish, however, from prostacyclin, for instance, in that they are more stable than prostacyclin. There are known already chemically relatively stable analogs of prostacyclin such as carbacyclin (which like the compounds of formula I contains the cis-bicyclo[3.3.0]octane moiety) but the activities of prior analogs are only of short duration when used in-vivo [c.f. Whittle et al., Prostaglandins 19 (1980), 605–627, especially page 623].

U.S. Pat. No. 4,306,076 (Example 13) discloses the E- and the Z-forms of 1,5-inter-m-phenylene-2,3,4-trinor-carbacyclin, i.e. of 3-(m-carboxybenzylidene)-6-beta-(3'S-hydroxy-1'E-octenyl)-7-alpha-hydroxy-cis-bicyclo[3.3.0]octane. The EZ-form of this compound (hereinafter referred to as "compound A") was used as an additional comparison compound in some of the tests described hereinafter. As can be seen from the test results, the compounds of formula I, especially those with $R_2$=cyclohexyl, also show superior effects in comparision to those produced by compound A.

SUMMARY OF THE INVENTION

It is the object of the present invention to provide new, pharmaceutically active cis-bicyclo[3.3.0]octane derivatives.

Another object of the invention is to provide cis-bicyclo[3.3.0]octane derivatives which exhibit a prolonged pharmaceutical activity in vivo.

It is also an object of the present invention to provide cis-bicyclo[3.3.0]octane derivatives which exhibit increased stability.

A further object of the present invention is to provide cis-bicyclo[3.3.0]octane derivatives which can be used to inhibit platelet aggregation without an accompanying blood pressure decrease.

An additional object of the present invention is to provide cis-bicyclo[3.3.0]octane derivatives which can be used to produce simultaneous inhibition of platelet aggregation and decrease in blood pressure.

Yet another object of the present invention is to provide a process for preparing cis-bicyclo[3.3.0]octane derivatives meeting the foregoing objects.

A still further object of the present invention is to provide pharmaceutical compositions for oral or parenteral administration containing cis-bicyclo[3.3.0]octane derivatives meeting the foregoing objects.

An additional object of the present invention is to provide improved methods of inhibiting blood platelet aggregation with and without simultaneously lowering the blood pressure using cis-bicyclo[3.3.0]octane derivatives.

These and other objects of the invention are acieved by providing cis-bicyclo[3.3.0]octane derivatives corresponding to the formula:

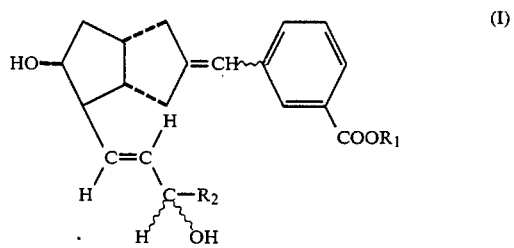

wherein
the phenyl radical has the EZ- or the E-configuration with respect to the double bond and at the carbon atom which carries the group $R_2$ the molecule has the RS- or S-configuration, and wherein $R_1$ represents hydrogen, a straight or branched alkyl radical containing 1 to 4 carbon atoms or a pharmaceutically acceptable cation, and $R_2$ represents cyclohexyl, 4-methylcyclohexyl or an 1-adamantyl group having the structure

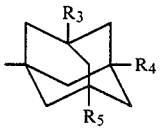

wherein $R_3$, $R_4$ and $R_5$ have the same or a different meaning and each represents hydrogen or methyl.

In another aspect of the invention, the objects are achieved by providing a process for preparing a cis-bicyclo[3.3.0]octane derivative comprising reacting a compound of the formula

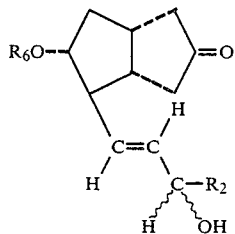

(II)

wherein $R_2$ represents cyclohexyl, 4-methylcyclohexyl or a 1-adamantyl group of the structure

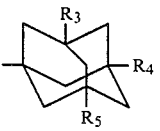

wherein $R_3$, $R_4$ and $R_5$ have the same or a different meaning and each represents hydrogen or methyl and wherein $R_6$ represents hydrogen or a protecting group cleavable under mild conditions in the absence of moisture and oxygen at about 0° C. to about 100° C. in presence of an aprotic solvent with a compound of the formula

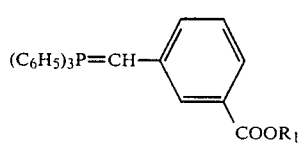

(III)

wherein $R_1$ represents hydrogen, a straight or branched alkyl radical containing 1 to 4 carbon atoms or a pharmaceutically acceptable cation and, if $R_6$ represents a protecting group, splitting off the protecting group under mild conditions.

In yet another aspect of the invention, the objects are achieved by providing a pharmaceutical composition comprising a therapeutically effective amount of a cis-bicyclo[3.3.0]octane derivative corresponding to the formula:

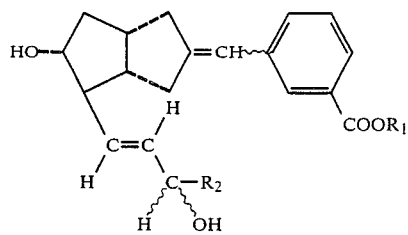

(I)

wherein the phenyl radical has the EZ- or the E-configuration with respect to the double bond and at the carbon atom which carries the group $R_2$ the molecule has the RS- or S-configuration, and wherein $R_1$ represents hydrogen, a straight or branched alkyl radical containing 1 to 4 carbon atoms or a pharmaceutically acceptable cation, and $R_2$ represents cyclohexyl, 4-methylcyclohexyl or a 1-adamantyl group having the structure

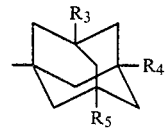

wherein $R_3$, $R_4$ and $R_5$ have the same or a different meaning and each represents hydrogen or methyl, and a pharmaceutically acceptable adjuvant.

In still another aspect of the invention, the objects are achieved by providing a method for inhibiting blood platelet aggregation in mammals comprising the step of administering an effective blood platelet aggregation inhibiting amount of a cis-bicyclo[3.3.0]octane derivative corresponding to the formula:

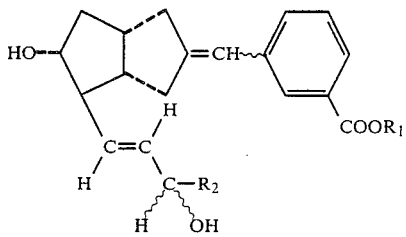

(I)

wherein the phenyl radical has the EZ- or the E-configuration with respect to the double bond and at the carbon atom which carries the group $R_2$ the molecule has the RS- or S-configuration, wherein $R_1$ represents hydrogen, a straight or branched alkyl radical containing 1 to 4 carbon atoms or a pharmaceutically acceptable cation, and $R_2$ represents cyclohexyl, 4-methylcyclohexyl or a 1-adamantyl group having the structure

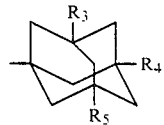

wherein

R$_3$, R$_4$ and R$_5$ have the same or a different meaning and each represents hydrogen or methyl.

Surprisingly the compounds of the present invention exhibit a considerably prolonged action in-vivo and also produce blood pressure lowering effects only after administering far higher dosages than those necessary to produce platelet aggregation inhibition. Accordingly the compounds of formula I can be used not only in diseases in which an inhibition of platelet aggregation is desired without accompanying lowering of the blood pressure (as for instance hyperaggregability in coronary heart disease) but also in higher doses in diseases in which a simultaneous vasodilation, i.e. a blood pressure lowering effect, is desired (as for instance ischaemic peripheral vascular disease).

DETAILED DESCRIPTION OF THE PREFERRED EMBODIMENTS

The compounds of formula I are prepared by reacting a compound of formula II

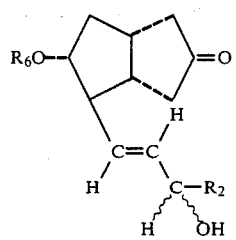

(II)

wherein

R$_2$ has the same meaning as in formula I and R$_6$ is a hydrogen atom or a protecting group which can easily be split off with a compound of formula III

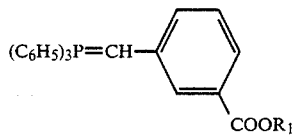

(III)

wherein

R$_1$ has the same meaning as above
and finally splitting off the group R$_6$ (if different from hydrogen) using mild conditions.

Preferred protecting groups represented by R$_6$ in the compound of formula II include the tetrahydropyranyl group or trialkylsilyl groups containing in the alkyl radicals, in total, from 3 to 6 carbon atoms (such as the trimethylsilyl- or the tert.-butyldimethylsilyl groups). Benzoyl- or p-phenylbenzoyl radicals and other protecting groups commonly used in prostaglandin chemistry may also be used as protecting group R$_6$.

The compound of formula II is reacted with the compound of formula III in presence of inert aprotic solvents such as benzene, toluene, dimethylsulfoxide or dimethylformamide and under an atmosphere of inert gases such as argon or nitrogen while carefully excluding moisture. The reaction may be carried out at temperatures between about 0° C. and about 100° C. Preferably benzene is used as the solvent at temperatures between 20° C. and 60° C. It is appropriate to add to the reaction mixture a small amount of a slightly acidic compound such as thiophenol or a substituted thiophenol like p-chlorothiophenol, thiocresol or similar compounds.

Thus the compounds of formula I having the EZ-configuration are obtained. In case R$_1$ is an alkyl radical, it is possible (prior to or after separation of the isomers) to saponify or hydrolyze the group COOR$_1$ to the carboxy group (R$_1$=H) and optionally to form a pharmaceutically acceptable salt of the compound. If, however, R$_1$ is hydrogen and there are desired compounds of formula I in which R$_1$ is an alkyl radical of 1 to 4 carbon atoms, it is also possible to esterify the compound having the free carboxylic group in a manner known per se.

The separation of the E- and Z-isomers may be effected by high performance liquid chromatography (HPLC) in a manner known per se using, for instance, a mixture of methanol/water (80:20) as solvent.

The compounds of formula III are obtained by reacting a phosphonium salt of the formula

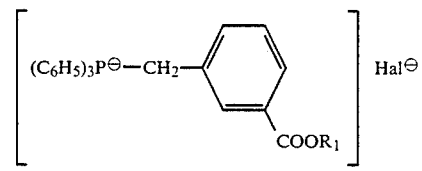

wherein R$_1$ has the same meaning as above and Hal is halogen such as chlorine or bromine [which salt can be prepared as described in the literature—c.f. Houben-Weyl "Methoden der organischen Chemie" Vol.5/4 (1960), page 337 or J.Am.Chem.Soc. 62 (1940) page 1180] in presence of dry solvents like benzene, toluene, dimethylsulfoxide, hexamethylphosphoric acid triamide, tetrahydrofuran and similar solvents at temperatures between about 0° C. to about 100° C., preferably 20° C. to 80° C., with a strong base such as potassium tert.-butoxide, methane sulfinyl-sodium, -potassium or -lithium and preferably sodium bistrimethylsilylamide. It is not necessary to isolate the compound of formula III from this reaction mixture prior to reacting it with the compound of formula II.

The starting compound of the general formula II, in which R$_6$ is hydrogen is prepared as outlined in the flow sheet on page 14 (where Z in all formulas has—with the exception of hydrogen—the same meaning as R$_6$ and where R$_2$ has the same meaning as above):

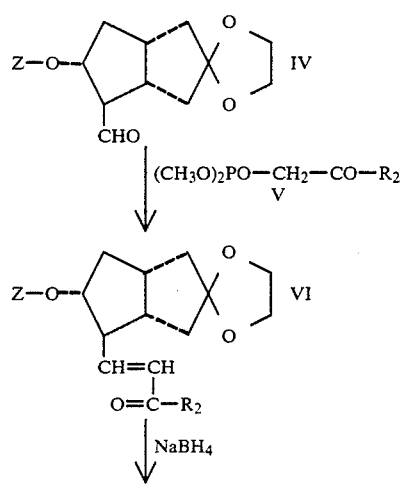

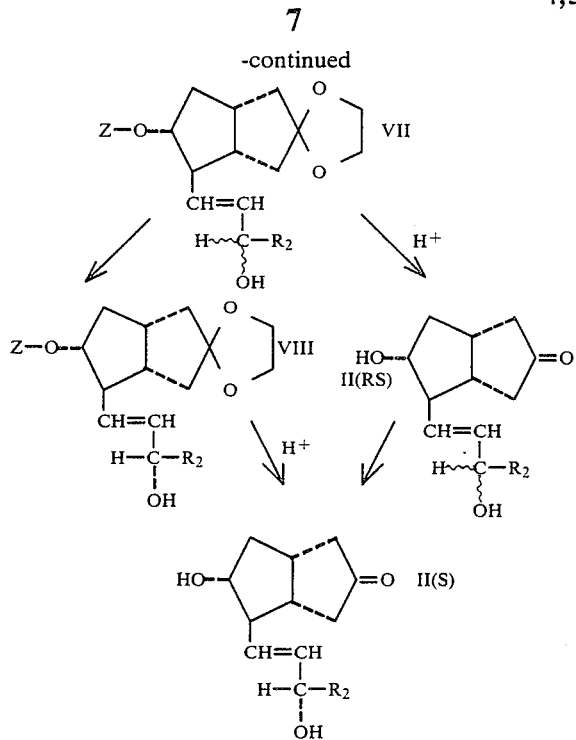

The following comments are given to explain the flow sheet:

The aldehyde IV in which, for instance, Z is the tert.-butyl dimethylsilyl group, i.e. the 3,3-ethylenedioxy-6-beta-formyl-7-alpha-tert.butyldimethylsilyloxy-cis-bicyclo[3.3.0]octane (Nicolaou et al., J. Chem.Soc., Chem.Commun. 1978, 1067) is reacted in a manner known per se with a phosphonate of the general formula V to give a ketone of the general formula VI. The reaction is effected in absence of moisture and oxygen in a solvent such as benzene, toluene, dimethoxyethane, dioxane or tetrahydrofuran at temperatures between about $-20°$ C. and $100°$ C., preferably $0°$ C. to $25°$ C., during about 2 to 24 hours.

The reduction of the keto compounds VI is effected by treatment with complex boron hydrides like sodium borohydride, preferably with addition of cerium(III) salts at temperatures between about $-40°$ C. and $60°$ C., preferably between $0°$ C. and $25°$ C.

If desired the mixture of the isomers (VII) may be separated into the S- and the R-isomers (the latter being without interest in the present invention) by column chromatography with silica gel and suitable solvents or mixtures thereof.

The protecting groups, i.e. the ketal group and the group Z (which preferably is the tert.-butyl dimethylsilyl group), are split off by treatment with a mixture of acetic acid/water/tetrahydrofuran (3:1:1) at about 25° C. [c.f. Corey et al., J.Am.Chem.Soc. 94 (1972) 6190; Nicolaou et al., loc.cit.]. Thus the S-forms of the compounds of formula II are obtained.

Naturally it is also possible to remove the protecting groups from the isomer mixture VII to give the RS-forms of the compounds of formula II [in the flow sheet designated "II(RS)"] which then may be separated into the S- and the R-isomers by column chromatography with silica gel. To prepare the RS-forms of the compounds of formula I the mixture II(RS) may be used as starting material which—optionally after introduction of a protecting group $R_6$—is reacted with the compound of formula III.

In case $R_6$ in the compound of formula II is desired to be one of the defined protecting groups, it is possible to selectively split the ethylendioxy group in a compound of formula VII or VIII, respectively. The same compound may, however, also be prepared by introducing the protecting group $R_6$ in the usual manner into a compound of formula II in which $R_6$ is hydrogen.

Inasmuch the compounds of formula I not only possess surprising and valuable long lasting biological properties but also a good-chemical stability, they may be used for parenteral and also for oral administration to humans and other mammals to produce an inhibition of blood platelet aggregation in therapy and prophylaxis of diseases in which blood platelet aggregation and/or a hyper-aggregability are of pathogenic importance. Such diseases include, for example, arterial thromboses in vascular endothelial disorders, atherosclerosis, hemostatic arterial and venous thromboses and myocardial infarction. Due to their influence on the blood pressure, the compounds of formula I are suitable also for the treatment of pulmonary as well as of systemic hypertension. The compounds of the invention are also useful for reducing platelet aggregability in artificial extracorporeal circulations and perfusion of isolated body portions (e.g., in dialysis, cardio-pulmonary bypass, transplantations etc.) wherein the compounds are added in micromolar concentrations to the patient's blood.

Futhermore, the compounds of formula I cause a decrease in the secretion of gastric acid. Accordingly, they may be used also in therapy and prophylaxis of diseases in which the secretion of gastric acid is increased (e.g. gastric ulcers or ulcus duodeni) as well as the therapy of ulcers having other origins (e.g. ulcers caused by the administration of antiphlogistics).

The invention accordingly also relates to medicaments or pharmaceutical compositions containing as active ingredients one or more of the heterocyclic compounds of formula I. The compound content of the individual dose is desirably between about 0.01 and 50 mg, whereby compositions for parenteral administration preferably contain about 0.01–10 mg and those for oral administration preferably contain about 0.1 to 50 mg. The medicaments for parenteral administration may be solutions or suspensions but may also be spray formulations for e.g. intranasal application or may be dry formulations suitable for easy reconstitution, as for instance, lyophylized sodium salts of compounds of formula I in single dosage form.

For oral administration, tablets, pills, dragees, capsules, and similar application forms including, for example, those from which the active ingredients have a delayed release are suitable. In the latter case it is also possible to increase the amount of the compound contained in the individual dose, for example to 100 or 250 mg for the single dosage form, provided that the rate of release of the active ingredient is such that the blood level does not exceed the level on oral adminstration of a normal dosage form without delayed release.

In production of these pharmaceutical compositions, generally used inorganic or organic adjuvants such as diluents, carriers, binders, lubricants and others are added to the compounds of the general formula I. The pharmaceutical compositions of the invention are prepared in accordance with accepted standards in a manner known per se. It should be mentioned that the compositions for parenteral use (beside the spray forms)

have to be sterile and in isotonic condition when in liquid form.

The following non-limiting examples serve further to illustrate the invention. No importance was attached to obtaining maximum yields in carrying out the experiments on which the examples are based. All temperature references are uncorrected.

The reactions were controlled by thin layer chromatography ("TLC") on plates precoated with silica gel ("Kieselgel 60" of E. Merck AG, Germany).

In column chromatography silica gel ("Kieselgel 60, 0.040–0.063 mm=230–400 mesh ASTM of Macherey—Nagel, Germany) was used unless otherwise indicated.

The ratio of the components of the solvent mixtures used in the chromatographic procedures is given in volume/volume.

The term "ether" as used in the examples means diethyl ether. The ether was distilled before use as a component in solvent mixtures for column chromatography.

The nuclear magnetic spectra were measured ($^1$H-spectra at 60 MHz, $^{13}$C-spectra at 15.08 MHz) with a commercially available Bruker, WP-60 NMR spectrometer. The chemical shifts are reported in ppm.

EXAMPLE 1

(a)
3,3-Ethylenedioxy-6β-(3′-oxo-3′-cyclohexyl-1′E-propenyl)-7α-tert.-butyl-dimethylsilyloxy-cis-bicyclo[3.3.0]octane (Formula VI:
  $R_2$=cyclohexyl
  Z=tert.-butyl-dimethylsilyl)

139 mg of dimethyl 2-oxo-2-cyclohexyl-ethane-phosphonate are dissolved in 2 ml of absolute dimethoxyethane and added dropwise, while stirring at room temperature and in an atmosphere of argon, to a suspension of 28.3 mg dispersed sodium hydride (50% dispersion in oil) in 15 ml of absolute dimethoxyethane, and the mixture is stirred for 45 minutes at room temperature. Thereafter, while stirring at room temperature in an atmosphere of argon, a solution of 194 mg of 3,3-ethylenedioxy-6β-formyl-7α-tert.-butyl-dimethylsilyloxy-cis-bicyclo[3.3.0]octane in 1 ml of absolute dimethoxyethane is added dropwise.

3 hours later a solution of 34.4 μl of glacial acetic acid in 400 μl of ether is added and then the mixture is evaporated in a vacuum. The slightly yellowish oily residue is dissolved in 10 ml of ether, washed with 5 ml of a saturated solution of sodium hydrogen carbonate and thereafter with 5 ml of a saturated solution of sodium chloride. The organic layer is dried over sodium sulfate and evaporated in a vacuum. The oily residue is further purified by column chromatography using ether/hexane (3:2) as solvent to give 188 mg (73% of the theoretical yield) of the title compound.

$C_{25}H_{42}SiO_4$: 434.702.

$^1$H-NMR (CDCl$_3$): 6.75 (2d, 1H); 6.15 (d, 1H); 3.93 (s, 4H); 3.89 (s, 1H); 0.95 (s, 9H); 0.8 (s, 6H).

(b)
3,3-Ethylenedioxy-6β-(3′S-hydroxy-3′-cyclohexyl-1′E-propenyl)-7α-tert.butyl-dimethylsilyloxy-cis-bicyclo[3.3.0]octane.

(Formula VIII:
  $R_2$=cyclohexyl
  Z=tert.butyl-dimethylsilyl)

1.36 g of the compound prepared according to Example 1a are dissolved in 18 ml of methanol. While stirring and chilling with ice 7.8 ml of a 0.4 molar solution of cerium-(III)-chloride in methanol is added followed by the addition in small amounts of 118.5 mg of sodium borohydride. The mixture is stirred for about 5 minutes in an ice bath and then for 30 minutes at room temperature. Thereafter 31 ml of pH7 buffer, 80 ml of dichloromethane and 50 ml of a saturated aqueous solution of potassium sodium tartrate are added, while stirring. The organic layer is separated and the aqueous layer is extracted three times with about 50 ml of dichloromethane each time. The combined organic layers are washed with about 25 ml of a saturated solution of sodium chloride, dried over sodium sulfate and evaporated in a vacuum.

The oily residue is purified by column chromatography using ether/petroleum ether (1:1) as eluent. Thus 516.2 mg (=38% of the theoretical yield) of the title compound, 111.4 mg of the 3R-isomer and 472.3 mg (35% of the theoretical yield) of the corresponding 3RS-form (i.e. the compound of formula VII) are obtained, which latter may be separated into the 3S- and 3R-isomer by a second column chromatographic treatment.

$C_{25}H_{44}SiO_4$: 436.718.

$^1$H-NMR (CDCl$_3$): 5.48 (m, 2H); 3.90 (s, 4H); 3.76 (m, 2H); 0.91 (s, 9H); 0.6 (s, 6H).

(c)
3-Oxo-6β-(3′S-hydroxy-3′-cyclohexyl-1′E-propenyl)-7α-hydroxy-cis-bicyclo[3.3.0]-octane (Formula II:
  $R_2$=cyclohexyl)

516.2 mg of the compound obtained according to Example 1b are stirred for 20 hours at room temperature with a mixture of 3 ml glacial acetic acid, 1 ml of tetrahydrofuran and 1 ml of water. The reaction is monitored by thin layer chromatography using the solvent system ether:acetone=2:1. After carefully adding 20 ml of a saturated aqueous solution of sodium hydrogen carbonate and of solid sodium hydrogen carbonate until the acetic acid is neutralized the mixture is extracted three times with 10 ml of dichloromethane each time. The combined organic layers are washed with 10 ml of a saturated solution of sodium chloride, then dried over sodium sulfate and finally evaporated in a vacuum.

The oily residue is purified by column chromatography (ether/acetone=2:1) to give 301 mg (=92% of the theoretical yield) of the desired compound as a colorless oil which at room temperature slowly solidifies.

Melting point: 96°–97.5° C.
$C_{17}H_{26}O_3$: 278.395.
$^1$H-NMR (CDCl$_3$): 5.48 (m, 2H); 3.88 (m, 2H).
$^{13}$C-NMR (methanol-d4): 222.52, 134.76, 133.78, 79.01, 78.34, 58.49, 46.63, 45.04, 44.31, 43.52, 42.43, 36.28, 30.01, 27.70, 27.21.

(d)
3-(m-Methoxycarbonylbenzylidene)-6β-(3′S-hydroxy-3′-cyclohexyl-1′E-propenyl)-7α-hydroxy-cis-bicyclo[3.3.0]octane.

(Formula I:
  $R_1$=CH$_3$
  $R_2$=cyclohexyl)

To a suspension of 2.141 g of sodium-bis-trimethylsilylamide in 20 ml of absolute benzene there are added at room temperature with exclusion of moisture and in an atmosphere of nitrogen, 5.743 g of m-methoxycarbonylbenzyl triphenyl phosphoniumbromide, while stirring. The mixture is stirred for 30 minutes at room temperature, heated to gentle boiling under reflux and allowed to cool to room temperature. After addition of a solution of 224.3 mg of the product obtained in Example 1c in 5 ml of absolute benzene and of 154 µl of thiophenol the mixture is stirred for one hour at room temperature and then for one week at 50°–60° C. (The progress of the reaction is monitored by thin layer chromatography using ether/ethyl acetate=4:1).

The reaction mixture is treated with 100 ml of water, the benzene layer is separated, and the aqueous layer is extracted three times with 25 ml of ether each time. The combined organic layers are washed with 25 ml of a saturated solution of sodium chloride, dried over sodium sulfate and evaporated in a vacuum.

The oily residue is purified by column chromatography (ether:ethyl acetate=4:1) to give 145 mg (=44% of the theoretical yield) of the 3EZ-form of the title compound in form of a colorless oil.

By high performance liquid chromatography under reversed phase conditions ["LiChrosorb RP 80" 10 µm (Knaur), column diameter 4.6 mm, flow speed 2 ml/min using methanol:water=8:2 as eluent] the Z- and E-isomers may be separated. Thus 65 mg of the 3EZ-mixture give 15.6 mg of the Z-isomer and 28.2 of the desired E-isomer of the title compound, which has a melting point of 126.5°–128° C. and gives the following spectral data:

$C_{26}H_{34}O_4$: 410.559.

$^1$H-NMR (CDCl$_3$): 7.77 (m, 2H); 7.32 (m, 2H); 6.37 (s broadened, 1H); 5.49 (m, 2H); 3.94 (s, 3H); 3.70 (m, 2H).

$^{13}$C-NMR (methanol-d4): 148.39, 140.30, 134.82, 134.33, 134.09, 131.23, 130.31, 129.40, 127.94, 122.58, 78.58, 78.34, 57.76, 52.59, 45.71, 45.04, 42.79, 41.15, 39.87, 38.90, 30.13, 27.70, 27.21.

(e)
3EZ-(m-carboxybenzylidene)-6β-(3'S-hydroxy-3'-cyclohexyl-1'E-propenyl)-7α-hydroxy-cis-bicyclo[3.3.0]octane (Formula I:
$R_1$=H
$R_2$=cyclohexyl)

145 mg of the compound (3EZ-form) obtained in Example 1d are dissolved in 5 ml of methanol and treated with 2 ml of 1N sodium hydroxide solution at room temperature for 2 hours, while stirring. (TLC solvent:ether/acetone=9:1). After standing for 15 hours at room temperature, 2.2 ml of 1N hydrochloric acid are added, while stirring, followed by extracting three times with 10 ml of dichloromethane each time. The combined extracts are washed with 10 ml of a saturated solution of sodium chloride, dried over sodium sulfate and evaporated in a vacuum.

Thus 106 mg (=76% of the theoretical yield) of the title compound are obtained in form of a colorless oil which slowly solidifies on standing at room temperature.

$C_{25}H_{32}O_4$: 396.532.

$^1$H-NMR (CDCl$_3$): 7.85 (m, 2H); 7.37 (m, 2H); 6.33 (s broadened, 1H); 5.46 (m, 2H); 3.67 (m, 2H); 3.08 (s, 3H, replaceable by treatment with D$_2$O).

(f) The sodium salt of the product of Example 1e may be prepared as follows:

70.2 mg of the carboxy compound of Example 1e are dissolved in 5 ml of methanol and treated with a solution of 29.8 mg of sodium hydrogen carbonate in 3 ml of water. After standing overnight, the mixture is heated for one hour to 60° C. The solution is evaporated in a vacuum, the residue is triturated with 10 ml of methanol and then again evaporated. The dry residue is extracted three times with 5 ml of methanol each time, the methanolic solution is filtered and the filtrate is evaporated in a vacuum. Thus 70.5 mg (=95% of the theoretical yield) of the desired sodium salt forming slightly yellowish crystals are obtained.

$C_{25}H_{31}O_4Na$: 418.514.

$^1$H-NMR (methanol-d4): 6.44 (s broadened, 1H); 5.49 (m, 2H).

EXAMPLE 2

3E-(m-Carboxybenzylidene)-6β-(3'S-hydroxy-3'-cyclohexyl-1'E-propenyl)-7α-hydroxy-cis-bicyclo[3.3.0]octane (Formula I:
$R_1$=H
$R_2$=cyclohexyl)

Following the procedure described in Example 1e but using 86 mg of the compound (3E-isomer) obtained in Example 1d, 12 ml of methanol and 3 ml of 1N sodium hydroxide solution, the title product is obtained as a colorless oil which solidifies slowly at room temperature. Yield: 78.5 mg=95% of the theoretical yield. Melting point: 161°–164° C.

$C_{25}H_{32}O_4$: 396.532.

$^1$H-NMR (CDCl$_3$): 7.90 (m, 2H); 7.43 (m, 2H); 6.37 (s broadened, 1H); 5.51 (m, 2H); 3.78 (m, 3H).

EXAMPLE 3

(a)
3,3-Ethylenedioxy-6β-[3'-oxo-3'-(1''-adamantyl)-1'E-propenyl]-7α-tert.butyl-dimethylsilyloxy-cis-bicyclo[3.3.0]octane (Formula VI:
$R_2$=1-adamantyl
Z=tert.butyl-dimethylsilyl)

242.6 mg of a sodium hydride dispersion (50% in oil) are mixed with 20 ml of absolute toluene and thereafter reacted with a solution of 1.47 g of dimethyl 2-oxo-2-(1'-adamantyl-)-ethane phosphonate in 40 ml of absolute toluene and with a solution of 1.5 g of 3,3-ethylendioxy-6β-formyl-7α-tert.butyl-dimethylsilyloxy-cis-bicyclo[3.3.0]octane in 5 ml of absolute toluene in the manner described in Example 1a. The reaction time in this case is, however, 6 hours at room temperature (while stirring), followed by 15 hours storage in an ice box. (TLC with ether:hexane=1:1).

Column chromatography with petrolether/ether (4:1) yields 999.1 mg (=45% of the theoretical yield) of the desired product.

$C_{29}H_{46}SiO_4$: 486.778.

$^1$H-NMR (CDCl$_3$): 6.61 (m, 2H); 3.88 (s, 4H); 3.76 (m, 1H); 0.88 (s, 9H); 0.03 (s, 6H).

The dimethyl 2-oxo-2-(1'-adamantyl)-ethane phosphonate used in this Example was obtained in the following manner:

77.5 ml of a solution of butyllithium (15% in hexane) are added dropwise with exclusion of moisture and in an atmosphere of nitrogen to 45 ml of dry ether, while stirring, followed by the addition of 10.8 ml of dimethyl methane phosphonate, dissolved in 50 ml of dry tetrahydrofuran. After stirring the mixture for another 15 minute period, a solution of 10.4 g of ethyl adamantyl-1-carboxylate in 50 ml of dry tetrahydrofuran is added dropwise at −75° C., and the mixture is stirred for 3 hours. The temperature is allowed by standing overnight in an ice box to reach 0° C. and then at this temperate the pH value of the mixture is adjusted to about 4–5 by carefully adding 4N hydrochloric acid. The solution is evaporated in a vacuum, the residue is dissolved in 100 ml of ethyl acetate and washed three times with 30 ml each time of a saturated aqueous solution of sodium chloride. The combined aqueous layers are twice extracted with 10 ml each time of ethyl acetate and then all ethyl acetate layers are combined, dried over sodium sulfate and evaporated in a vacuum. The oily residue is distilled to give 10.4 g of the desired ester (72% of the theoretical yield) in form of a colorless oil boiling at 0.2 mm Hg and 170°–171° C.

$^1$H-NMR (CDCl$_3$): 3.86 (s, 3H); 3.67 (s, 3H); 3.31 (s, 1H); 2.96 (s, 1H); 1.94 (m,15H).

(b)
3,3-Ethylenedioxy-6β-[3′S-hydroxy-3′-(1″-adamantyl)-1′E-propenyl]-7α-tert.butyl-dimethylsilyloxy-cis-bicyclo[3.3.0]octane (Formula VIII:
  R$_2$ = 1-adamantyl
  Z = tert.butyl-dimethylsilyl)

By using the procedure described in Example 1b and 422.5 mg of the product obtained in Example 3a, dissolved in 5 ml of methanol, 2.6 ml of a 0.4 molar solution of cerium-(III)-chloride in methanol and 51.3 mg of sodium borohydride after column chromatography with petroleum ether/ether (2:1) as eluent there are obtained 314.1 mg (=74% of the theoretical yield) of the title compound and 56.9 mg of the 3′R-isomer, which is dicarded.

C$_{29}$H$_{48}$SiO$_4$: 488.794.

3′S-isomer: $^1$H-NMR (CDCl$_3$): 5.50 (m, 2H); 3.93 (s, 4H); 3.70 (m, 2H); 0.93 (s, 9H); 0.08 (s, 6H).

$^{13}$C-NMR (methanol-d4): 134.88, 130.37, 119.97, 82.05, 80.28, 65.37, 64.76, 58.07, 43.95, 43.10, 42.49 40.91, 39.26, 38.29, 37.80, 36.77, 29.58, 26.48, 18.81.

(c)
6β-[3′S-Hydroxy-3′-(1″-adamantyl)-1′E-propenyl]-7α-hydroxy-cis-bicyclo[3.3.0]-octane-3-one (Formula II:
  R$_2$ = 1-adamantyl)

On following the procedure described in Example 1c there are obtained from 314.1 mg of the product of Example 3b after column chromatography (using ether:acetone=3:1 as eluent) 192,2 mg of the desired compound in form of white crystals, melting at 142°–143.5° C. after recrystallization from diisopropylether.

C$_{21}$H$_{30}$O$_3$: 330.471.

$^1$H-NMR (CDCl$_3$): 5.52 (m, 2H); 3.95 (m, 1H); 3.53 (m, 1H).

(d)
3EZ-(m-Methoxycarbonylbenzylidene)-6β-[3′S-hydroxy-3′-(1″-adamantyl)-1′E-propenyl]-7α-hydroxy-cis-bicyclo[3.3.0]octane.

(Formula I:
  R$_1$ = CH$_3$
  R$_2$ = 1-adamantyl)

By using 195.9 mg of the product obtained in Example 3c, 2.91 g of m-methoxycarbonylbenzyl triphenyl phosphoniumbromide and 1.09 g of sodium-bis-trimethylsilyl-amide as reactants in the procedure described in Example 1d there are obtained after column chromatography (using ether:acetone=4:1 as eluent) 114.4 mg (=42% of the theoretical yield) of the title compound in solid form.

$^1$H-NMR (CDCl$_3$): 7.86 (m, 2H); 7.36 (m, 2H); 6.35 (s broadened, 1H); 5.50 (m, 2H); 3.88 (s, 3H); 3.80 (m, 2H).

(e)
3EZ-(m-Carboxybenzylidene)-6β-[3′S-hydroxy-3′-(1″-adamantyl)-1′E-propenyl]-7α-hydroxy-cis-bicyclo[3.3.0]octane (Formula I:
  R$_1$ = H
  R$_2$ = 1-adamantyl)

The procedure is the same as described in Example 1e, whereby, however, 110.4 mg of the product obtained in Example 3d, dissolved in 10 ml of methanol, and 3 ml of 1N sodium hydroxide solution are used as the reactants. Thus 79.3 mg of the title compound (=74% of the theoretical yield) are obtained in solid form.

C$_{29}$H$_{36}$O$_4$: 448.609.

$^1$H-NMR (CDCl$_3$): 7.83 (m, 2H); 7.37 (m, 2H); 6.37 (s broadened, 1H); 5.48 (m, 2H); 3.47 (m, 2H); 3.25 (s, 3H, replaceable by treatment with D$_2$O).

EXAMPLE 4

By using the appropriate reactants and otherwise proceeding as described in the preceding examples, there are obtained:

(a)
3E-(m-Ethoxycarbonyl-benzylidene)-6β-(3′S-hydroxy-3′-cyclohexyl-1′E-propenyl)-7α-hydroxy-cis-bicyclo[3.3.0]octane (Formula I:
  R$_1$ = C$_2$H$_5$
  R$_2$ = cyclohexyl)
C$_{27}$H$_{36}$O$_4$: 424.586.
Melting point: 115°–116° C.

$^1$H-NMR (CDCl$_3$): 7.78 (m, 2H); 7.30 (m, 2H); 6.31 (s broadened, 1H); 5.48 (m, 2H); 4.23 (q, 2H); 3.70 (m, 2H); 1.38 (t).

(b)
3E-[m-(n-Propyloxycarbonyl)-benzylidene]-6β-(3′S-hydroxy-3′-cyclohexyl-1′E-propenyl)-7α-hydroxy-cis-bicyclo[3.3.0]octane (Formula I:
  R$_1$ = n-C$_3$H$_7$
  R$_2$ = cyclohexyl)
C$_{28}$H$_{38}$O$_4$: 438.613.
Melting point: 68°–71° C.

$^1$H-NMR (CDCl$_3$): 7.78 (m, 2H); 7.32 (m, 2H); 6.33 (s broadened, 1H); 5.43 (m, 2H); 4.23 (t, 2H); 3.64 (m, 2H).

(c) Sodium salt of
3E-(m-carboxylbenzylidene)-6β-(3′S-hydroxy-3′-cyclohexyl-1′E-propenyl)-7α-hydroxy-cis-bicyclo[3.3.0]octane (Formula I:
  R$_1$ = Na
  R$_2$ = cyclohexyl)
C$_{25}$H$_{31}$O$_4$Na: 418.514.

¹H-NMR (methanol-d4): 6.44 (s broadened, 1H); 5.51 (m, 2H).

(d)
3E-(m-Carboxybenzylidene)-6β-[3'S-hydroxy-3'-(adamantyl-1'')-1'E-propenyl]-7α-hydroxy-cis-bicyclo[3.3.0]octane (Formula I:
  R₁=H
  R₂=adamantyl)
C₂₉H₃₆O₄: 448.609.
¹H-NMR (methanol-d4): 7.78 (m, 2H); 7.37 (m, 2H); 6.38 (s broadened, 1H); 5.50 (m, 2H).

(e)
3EZ-(m-Carboxybenzylidene)-6β-[3'S-hydroxy-3'-(3'',5''-dimethyladamantyl-1'')-1'E-propenyl]-7α-hydroxy-cis-bicyclo[3.3.0]octane (Formula I:
  R₁=H;
  R₂=3,5-dimethyladamantyl-1)

(f)
3E-[m-(tert.-Butyloxycarbonyl)-benzylidene]-6β-(3'S-hydroxy-3'-cyclohexyl-1'E-propenyl)-7α-hydroxy-cis-bicyclo[3.3.0]octane (Formula I:
  R₁=(CH₃)₃C-
  R₂=cyclohexyl)

(g)
3E-(m-Carboxybenzylidene)-6β-[3'S-hydroxy-3'-(4''-methylcyclohexyl)-1'E-propenyl]-7α-hydroxy-cis-bicyclo[3.3.0]octane (Formula I:
  R₁=H;
  R₂=4-methylcyclohexyl)

(h) Potassium salt of
3E-(m-carboxybenzylidene)-6β-(3'S-hydroxy-3'-cyclohexyl-1'E-propenyl)-7α-hydroxy-cis-bicyclo[3.3.0]octane (Formula I:
  R₁=K
  R₂=cyclohexyl)
and other compounds of formula I.

The valuable properties of the compounds of formula I are demonstrated by the following test results.

The enzyme adenylate cyclase catalyzes the formation of adenosine 3',5'-cyclic monophosphate (c-AMP) from adenosine triphosphate (ATP). If the adenylate cyclase in thrombocytes is stimulated by substances like prostacyclin, the c-AMP content of the thrombocytes is considerably increased whereby an aggregation of the thrombocytes is prevented. The following table 1 shows the degrees of stimulation of adenylate cyclase in horse thrombocytes induced by some of the compounds of formula I in comparison to the effects caused by 5,6-dihydroprostacyclin or by compound A, respectively:

TABLE 1

| Test compound | EC*₂₀₀% [μMol/l] | relative activity |
|---|---|---|
| 5,6-Dihydroprostacyclin | 15.0 | 1.0 |
| Compound A | 0.4 | 37.5 |
| Example 1e | 0.15 | 100.0 |
| Example 2 | 0.13 | 115.4 |

TABLE 1-continued

| Test compound | EC*₂₀₀% [μMol/l] | relative activity |
|---|---|---|
| Example 3e | 0.18 | 83.3 |

*Dose causing a threefold stimulation of the c-AMP formation from ATP.

The aggregation of human thrombocytes induced by arachidonic acid may be prevented e.g. by prostacyclin. The following Table 2 shows the values of the IC₅₀ (i.e. the concentration which under the experimental conditions causes inhibition of the platelet aggregation in 50% of the cases) and also the relative activity in comparison to prostacyclin for some known compounds and for the products of Examples 1e and 2:

TABLE 2

| Test compound | IC₅₀ [μMol/l] | relative activity |
|---|---|---|
| Prostacyclin | 0.0078 | 1.0 |
| 5,6-Dihydroprostacyclin | 0.18 | 0.043 |
| Compound A | 0.12 | 0.065 |
| Example 1e | 0.08 | 0.098 |
| Example 2 | 0.07 | 0.11 |

In addition reference is made to the findings of Whittle et al. (loc. cit., page 611) that carbacyclin is only 0.02 times as active as prostacyclin as an inhibitor of the platelet aggregation induced by arachidonic acid in vitro.

Table 3 shows the activity of certain test compounds on the ADP induced fall in platelet count in-vivo in narcotized rats (urethane narcosis) on intravenous administration of the test compounds.

TABLE 3

| Test compound | relative activity |
|---|---|
| 5,6-Dihydroprostacyclin | 1.0 |
| Compound A | 0.1 |
| Example 1e | 1.0 |
| Example 2 | 1.0 |

Tables 1 to 3 demonstrate the good blood platelet aggregation inhibiting effect of the compounds of formula I. As already mentioned herein before, these compounds produce blood pressure lowering effects only after administering far higher dosages then those necessary to produce platelet aggregation inhibition as may be seen from the following Tables 4a and 4b (the ED₂₀ is the dose causing a drop of the diastolic blood pressure by 20 mm Hg):

TABLE 4a

Blood pressure lowering activity in conscious, spontaneous hypertensive rats (measurement via indwelling catheter, intravenous administration of the test compounds):

| Test compound | ED₂₀ mg/kg | relative activity |
|---|---|---|
| 5,6-Dihydroprostacyclin | 0.005 | 1.0 |
| Compound A | 1.9 | 0.003 |
| Example 1e | 0.073 | 0.068 |
| Example 2 | 0.094 | 0.053 |
| Example 3e | >1.0 | <0.005 |

TABLE 4b

Blood pressure lowering activity in narcotized rats (pentobarbital narcosis; intravenous administration of the test compounds):

| Test compound | ED$_{20}$ mg/kg | relative activity |
| --- | --- | --- |
| Prostacyclin | 0.16 | 1.0 |
| Example 2 | 5.39 | 0.03 |

Both prostacyclin and carbacyclin are rapidly metabolized in-vivo to inactive compounds and accordingly exhibit aggregation inhibiting and blood pressure lowering activities only for a short time. Surprisingly, the compounds of formula I produce considerably longer lasting effects than said known compounds as may be seen from the following Tables 5 and 6:

TABLE 5

On intravenous administration of a supramaximal hypotensive dose (1 mg/kg) of the test compounds in narcotized rats (pentobarbital narcosis) the following persistence characteristics of the blood pressure lowering activity ("b.p.l.a.") were observed:

| Test compound | rate of decay in % per min. | half time of b.p.l.a. |
| --- | --- | --- |
| Prostacyclin | 11 | 5.89 min |
| Example 2 | 2.6 | 25.96 min |

As can be seen from Table 5, the product of Example 2 acts about 5 times longer than prostacyclin. Also with respect to the thrombocyte aggregation inhibiting activity, the considerably extended duration of the effect could be demonstrated. In this experiment the product obtained in Example 2 was administered orally in a dose of 4.64 mg/kg of narcotized rats (urethane narcosis). The thrombocyte aggregation inhibiting activity was determined at 30, 60 and 150 minutes after administration of the compound (Method: ADP induced fall in thrombocyte count in-vivo, determined by a "Technicon Autocounter").

TABLE 6

| | Time after administration (min) | | |
| --- | --- | --- | --- |
| | 30 | 60 | 150 |
| % inhibition of platelet aggregation | 38 | 26 | 22 |

Oral administration of the product of Example 2 thus causes a strong thrombocyte aggregation inhibition for at least 2.5 hours, whereas prostacyclin and related compounds are known to be ineffective on oral administration.

The foregoing description and examples have been set forth merely to illustrate the invention and are not intended to be limiting. Since modifications of the described embodiments incorporating the spirit and substance of the invention may occur to persons skilled in the art, the scope of the invention is to be limited solely with respect to the appended claims and equivalents.

We claim:

1. Cis-bicyclo[3.3.0]octane derivatives corresponding to the formula:

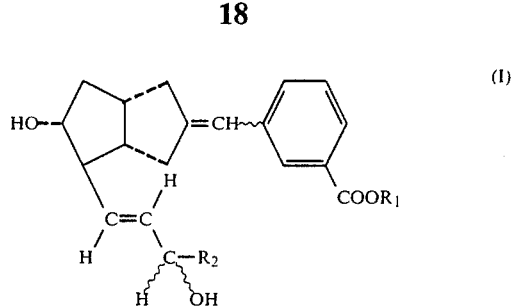

wherein
the phenyl radical has the EZ- or the E-configuration with respect to the double bond and at the carbon atom which carries the group R$_2$ the molecule has the RS- or S-configuration, and wherein
R$_1$ represents hydrogen, a straight or branched alkyl radical containing 1 to 4 carbon atoms or a pharmaceutically acceptable cation, and
R$_2$ represents cyclohexyl, 4-methylcyclohexyl or an 1-adamantyl group having the structure

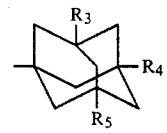

wherein R$_3$, R$_4$ and R$_5$ have the same or a different meaning and each represents hydrogen or methyl.

2. A cis-bicyclo[3.3.0]octane derivative according to claim 1, wherein R$_2$ represents

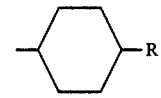

wherein R represents hydrogen or methyl.

3. A cis-bicyclo[3.3.0]octane derivative according to claim 1, wherein R$_1$ represents a methyl or an ethyl radical.

4. A cis-bicyclo[3.3.0]octane derivative according to claim 1 wherein R$_1$ represents a sodium or a potassium cation.

5. A cis-bicyclo[3.3.0]octane derivative according to claim 1, which is the 3'S-isomer of said derivative.

6. A cis-bicyclo[3.3.0]octane derivative according to claim 1, comprising 3-(m-carboxybenzylidene)-6-beta-(3'S-hydroxy-3'-cyclohexyl-1'E-propenyl)-7-alpha-hydroxy-cis-bicyclo[3.3.0]octane having the formula

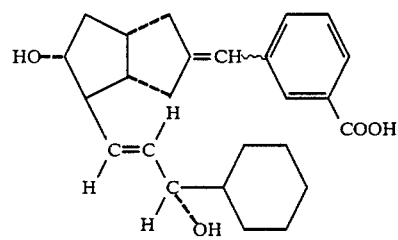

and having the 3EZ or 3E-configuration and its pharmaceutically acceptable salts.

7. A cis-bicyclo[3.3.0]octane derivative according to claim 6, comprising the sodium salt of said derivative.

8. A process for preparing a cis-bicyclo[3.3.0]octane derivative comprising reacting a compound of the formula:

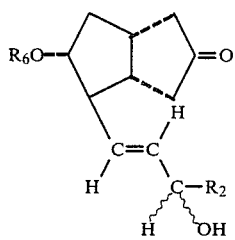 (II)

wherein
R$_2$ represents cyclohexyl, 3-methylcyclohexyl or a 1-adamantyl group of the structure

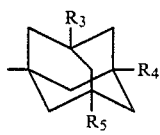

ps wherein
R$_3$, R$_4$ and R$_5$ have the same or a different meaning and each represents hydrogen or methyl and wherein R$_6$ represents hydrogen or a protecting group cleavable under mild conditions
in the absence of moisture and oxygen at about 0° C. to about 100° C. in an aprotic solvent with a compound of the formula

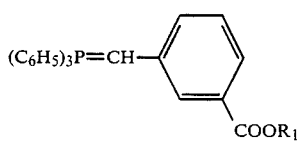 (III)

wherein
R$_1$ represents hydrogen, a straight or branched alkyl radical containing 1 to 4 carbon atoms or a pharmaceutically acceptable cation
and, if R$_6$ represents a protecting group, splitting off the protecting group under mild conditions.

9. A process according to claim 8, wherein a compound of formula II is reacted with a compound of formula III in the presence of a slightly acidic compound.

10. A process according to claim 9, wherein said slightly acidic compound is selected from the group consisting of thiophenol and substituted thiophenols.

11. A process according to claim 8, wherein R$_1$ represents an alkyl group containing 1 to 4 carbon atoms, further comprising the step of saponifying the group COOR$_1$ in the compound of formula I.

12. A process according to claim 8, wherein R$_1$ represents hydrogen, further comprising the step of transforming the group R$_1$ into a pharmaceutically acceptable cation by treatment with an appropriate basic compound.

13. A process according to claim 11, further comprising the step of transforming the group R$_1$ in the saponified compound into a pharmaceutically acceptable cation by treatment with an appropriate basic compound.

14. A process according to claim 12, wherein said basic compound is sodium hydrogen carbonate.

15. A process according to claim 13, wherein said basic compound is sodium hydrogen carbonate.

16. A pharmaceutical composition comprising a therapeutically effective amount of a cis-bicyclo[3.3.0]octane derivative corresponding to the formula

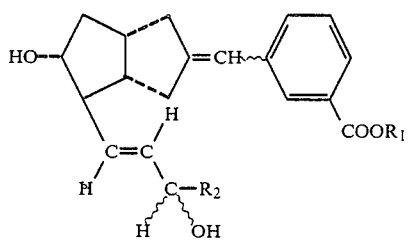 (I)

wherein
the phenyl radical has the EZ- or the E-configuration with respect to the double bond and at the carbon atom which carries the group R$_2$ the molecule has the RS- or S-configuration, and wherein
R$_1$ represents hydrogen, a straight or branched alkyl radical containing 1 to 4 carbon atoms or a pharmaceutically acceptable cation, and
R$_2$ represents cyclohexyl, 4-methylcyclohexyl or a 1-adamantyl group having the structure

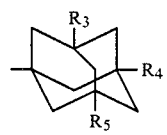

wherein
R$_3$, R$_4$ and R$_5$ have the same or a different meaning and each represents hydrogen or methyl,
and a pharmaceutically acceptable adjuvant.

17. A pharmaceutical composition according to claim 16 wherein the therapeutically effective amount of the cis-bicyclo[3.3.0]octane derivative is from about 0.01 to about 50 mg per individual dose.

18. A pharmaceutical composition according to claim 16, suitable for parenteral administration and containing per individual dose from about 0.01 to about 10 mg of said cis-bicyclo[3.3.0]octane derivative in sterile solid form or in a sterile solution or suspension in a pharmaceutically acceptable carrier.

19. A pharmaceutical composition according to claim 16, suitable for oral administration and containing per individual dose from about 0.1 to about 50 mg of said cis-bicyclo[3.3.0]octane derivative in a form selected from the group consisting of capsules, dragees and tablets.

20. A pharmaceutical composition according to claim 16, suitable for oral administration containing a therapeutically effective amount of said cis-bicyclo[3.3.0]octane derivative and at least one pharmaceutically acceptable inert carrier or diluent.

21. A pharmaceutical composition according to claim 16, suitable for oral administration comprising capsules, dragees or tablets from which the active ingredients show a delayed release, containing per individual dose from about 0.1 to about 250 mg of said cis-bicyclo[3.3.0]octane derivative.

22. A method for inhibiting blood platelet aggregation in mammals comprising the step of administering an effective blood platelet aggregation inhibiting amount of a cis-bicyclo[3.3.0]octane derivative corresponding to the formula:

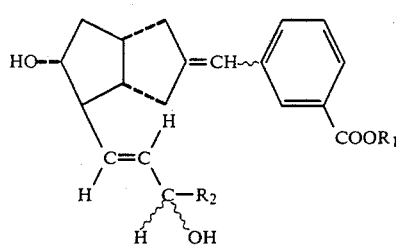
(I)

wherein
the phenyl radical has the EZ- or the E-configuration with respect to the double bond and at the carbon atom which carries the group $R_2$ the molecule has the RS- or S-configuration, and wherein
$R_1$ represents hydrogen, a straight or branched alkyl radical containing 1 to 4 carbon atoms or a pharmaceutically acceptable cation, and
$R_2$ represents cyclohexyl, 4-methylcyclohexyl or a 1-adamantyl group have the structure

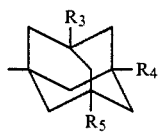

wherein
$R_3$, $R_4$ and $R_5$ have the same or a different meaning and each represents hydrogen or methyl.

23. A method for inhibiting blood platelet aggregation in mammals according to claim 22 and simultaneously lowering blood pressure, wherein the administered amount of cis-bicyclo[3.3.0]octane derivative is sufficient to simultaneously inhibit blood platelet aggregation and lower the blood pressure.

24. A method for decreasing the secretion of gastric acid in mammals comprising the step of administering an effective gastric acid secretion reducing amount of a cis-bicyclo[3.3.0]octane derivative corresponding to the formula:

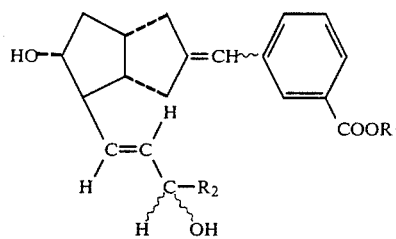
(I)

wherein
the phenyl radical has the EZ- or the E-configuration with respect to the double bond and at the carbon atom which carries the group $R_2$ the molecule has the RS- or S-configuration, and wherein
$R_1$ represents hydrogen, a straight or branched alkyl radical containing 1 to 4 carbon atoms or a pharmaceutically acceptable cation, and
$R_2$ represents cyclohexyl, 4-methylcyclohexyl or a 1-adamantyl group having the structure

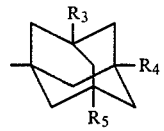

wherein
$R_3$, $R_4$ and $R_5$ have the same or a different meaning and each represents hydrogen or methyl.

25. A cis-bicyclo[3.3.0]octane derivative according to claim 1, wherein $R_1$ represents a hydrogen atom.

* * * * *

UNITED STATES PATENT OFFICE
CERTIFICATE OF CORRECTION

PATENT NO. : 4,510,323
DATED : April 9, 1985
INVENTOR(S) : Horst R.E. BOEHLKE; Gerriet K.H. LOSCHEN;
Gudrun E. MICHEL and Bernd MUELLER It is certified that error appears in the above-identified patent and that said Letters Patent are hereby corrected as shown below:

IN THE SPECIFICATION:

At Column 2, line 49, please delete "acieved" and insert in lieu thereof --achieved--;

At Column 8, line 12, please delete "good-chemical" and insert in lieu thereof --good chemical--;

At Column 17, line 38, please delete "of" (second occurrence) and insert in lieu thereof --to--.

IN THE CLAIMS:

At Column 19, Claim 8, line 16, delete "3-methylcyclohexyl" and insert in lieu thereof --4-methylcyclohexyl--;
line 25, delete "ps wherein" and insert in lieu thereof --wherein--.

At Column 21, Claim 22, line 24, delete "have" and insert in lieu thereof --having--.

Signed and Sealed this

Seventeenth Day of December 1985

[SEAL]

Attest:

DONALD J. QUIGG

Attesting Officer    Commissioner of Patents and Trademarks